United States Patent [19]

Edwards

[11] Patent Number: 5,505,730
[45] Date of Patent: Apr. 9, 1996

[54] THIN LAYER ABLATION APPARATUS

[75] Inventor: Stuart D. Edwards, 1681 Austin Ave., Los Altos, Calif. 94024

[73] Assignee: Stuart D. Edwards, Los Altos, Calif.

[21] Appl. No.: 265,459

[22] Filed: Jun. 24, 1994

[51] Int. Cl.$^6$ ........................................... A61B 17/36
[52] U.S. Cl. .............................. 606/41; 606/28; 606/192; 606/193; 604/21; 607/116
[58] Field of Search ..................... 606/27–31, 41, 606/46–50, 191–194; 607/100–105, 115, 116; 604/20, 21, 53, 96–103

[56] References Cited

U.S. PATENT DOCUMENTS

| | | |
|---|---|---|
| 1,620,929 | 3/1927 | Wallerich . |
| 1,827,306 | 10/1931 | Chapman et al. . |
| 3,645,265 | 2/1972 | Majzlin . |
| 3,840,016 | 10/1974 | Lindemann . |
| 3,924,628 | 12/1975 | Droegemueller et al. . |
| 3,948,270 | 4/1976 | Hasson . |
| 4,057,063 | 11/1977 | Gieles et al. . |
| 4,676,258 | 6/1987 | Inokuchi et al. . |
| 4,799,479 | 1/1989 | Spears ........................................ 606/7 |
| 4,865,047 | 9/1989 | Chou et al. . |
| 4,949,718 | 8/1990 | Neuwirth et al. . |
| 4,960,133 | 10/1990 | Hewson . |
| 4,961,435 | 10/1990 | Kitagawa et al. . |
| 4,979,948 | 12/1990 | Geddes et al. . |
| 5,084,044 | 1/1992 | Quint . |
| 5,186,181 | 2/1993 | Franconi et al. . |
| 5,188,122 | 2/1993 | Phipps et al. . |
| 5,191,883 | 3/1993 | Lennox et al. ........................... 606/27 |
| 5,232,444 | 8/1993 | Just et al. ................................. 604/53 |
| 5,236,413 | 8/1993 | Feiring ..................................... 604/21 |
| 5,277,201 | 1/1994 | Stern . |

OTHER PUBLICATIONS

Singer, et al.; *Preliminary Clinical Experience With A Thermal Balloon Endometrial Ablation Method To Treat Menorrhagia*; Obstetrics & Gynecology, vol. 83, No. 5, Part 1, May 1994; pp. 732–734.

Phipps, et al.; *Treatment Of Functional Menorrhagia By Radiofrequency–induced Thermal Endometrial Ablation*; The Lancet, vol. 335; Feb. 17, 1990; pp. 374–376; United Kingdom.

Phipps, et al.; *Experimental And Clinical Studies With Radiofrequency–Induced Thermal Endometrial Ablation For Functional Menorrhagia*; Obstetrics & Gynecology, vol. 76, No. 5, Part. 1, Nov. 1990; pp. 876–881; United Kingdom.

Prior, et al.; *Treatment Of Menorrhagia By Radiofrequency Heating*; l Int. J. Hyperthermia, 1991, vol. 7, No. 1, 22–230; pp. 213–216; United Kingdom.

Mumford, et al.; *Sterilization Needs In The 1990's: The Case For Quinacrine Nonsurgical Female Sterilization*; American Journal of Obstetrics & Gynecology, vol. 167, No. 5, Nov. 1992; pp. 1203–1207; United Kingdom.

Neuwirth, et al.; *The Endometrial Ablator: A New Instrument*; Obstetrics & Gynecology vol. 83, No. 5, Part 1, May 1994; pp. 792–796.

*Primary Examiner*—Stephen C. Pellegrino
*Assistant Examiner*—Michael Peffley
*Attorney, Agent, or Firm*—Haynes & Davis

[57] ABSTRACT

An ablation apparatus has a balloon that is inserted into an organ of a body and ablates all or a selected portion of the inner layer of the organ. Electrolytic solution fills the balloon, and the balloon includes a plurality of apertures from which electrolytic solution flows from the balloon. The flow rate of electrolytic solution is dependent on the pressure applied to the balloon by the electrolytic solution. A conforming member, with a conductive surface and a back side, is made of a material that substantially conforms to a shape of the inner layer of the organ and delivers the electrolytic solution and RF energy through the conductive surface to the inner layer. Advantageously, difficult to access areas are reached with the inclusion of the conforming member. Optionally positioned between the conforming member and the balloon is a porous membrane. A printed circuit is printed in or on the conforming member and delivers RF energy to selected sections of the inner layer. The printed circuit provides for the monitoring of impedance, temperature and circuit continuity. Additionally, the printed circuit can be multiplexed.

29 Claims, 9 Drawing Sheets

THIN LAYER ABLATION APPARATUS

BACKGROUND OF THE INVENTION

1. Field of the Invention

This invention relates generally to an ablation apparatus for the selective ablation of the inner layers of body organs, and more particularly, to the endometrium layer of the uterus.

2. Description of Related Art

There are a number of body organs, including but not limited to the uterus, gall bladder, large intestine and the like, that have inner layers which have abnormal conditions. Traditional methods of treatment have included removal of the body organ to treat the abnormal condition, the use of lasers, and the application of a thermal source.

A diseased condition of the uterus, menorrhagia, is defined as excessive menstrual bleeding in the absence of organic pathology. It has no known aetiology and it has been postulated that it is due to an inappropriate exposure of the endometrium to hormones. Menorrhagia is an exceedingly common problem, typically comprising approximately one in five outpatient referrals to gynecological departments. Women suffering severe menorrhagia are at risk from chronic anemia. The first treatment employed may be the administration of drug therapy. A major disadvantage is the need to administer drugs long term, and frequently the beneficial effects are only temporary. Another treatment is hysterectomy.

A number of physical and chemical methods have been tried as alternatives to hysterectomy, including the use of superheated steam, cryotherapy, urea injection and radium packing. The most commonly used methods as an alternative to hysterectomy are, ablation of the endometrium either by using a laser, such as a Nd:YAG laser, or the use of RF energy applied with an electrode.

Laser treatments have provided only limited success. RF is an attractive alternative. In RF heating, a conductive probe is placed within the uterine cavity and an insulated ground-plane electrode or belt is placed around the patient's midriff. RF energy is applied to the thermal probe with the external belt electrode acting as the return arm of the circuit. The electrical load presented by the RF thermal probe, patient, and external belt is matched to the output of the RF generator via a tuning unit, to form a series resonant circuit. Once tuned, the majority of the power applied to the probe is deposited into the endometrium as heat.

Current flows primarily capacitively, and an electric field is set up around the active tip of the probe. Tissue lying within the field becomes heated because of rapid oscillation of charged particles and locally induced currents.

Prior et al. have reported on the use of RF to treat menorrhagia. Power at 27·12 MHz was delivered to a probe that was placed into the uterine cavity and capacitively coupled to a second electrode consisting of a belt placed around the patient, Prior et al., Int. J. Hyperthermia, 1991, Vol. 7, No.2, pgs 213 to 220. The active electrode was a 10 mm diameter stainless-steel cylinder with a length of 70 mm. This method, however, did not adequately deliver RF energy to the entire endometrium. Because the endometrium has an irregular surface, it is difficult to deliver sufficient RF energy to the entire structure and effective treat menorrhagia.

However, it is preferable if there is direct contact in order to treat the entire endometrium surface. In U.S. Pat. No. 5,277,201 (the "'201 patent") an electroconductive, expandable balloon expands the interior of the uterus and effects electrical contact with the endometrial lining to be destroyed. The device of the '201 patent fails, however, to provide sufficient physical contact with the entire endometrium, and thus the treatment is not complete. Not only is the physical contact with the endometrium unsatisfactory, but the effective delivery of RF energy to the endometrium could be improved.

There is a need for an RF ablation apparatus that provides more suitable conformation with a lining of a body organ, such as the endometrium of the uterus. Additionally, there is a need for the effective delivery of RF energy to the endometrium as well as other interior layers of body organs.

SUMMARY OF THE INVENTION

An object of the invention is to provide an ablation apparatus suitable for interior thin walled areas of body organs.

Another object of the invention is to provide an ablation apparatus that effectively conforms to the shape of the interior of a body organ.

Yet another object of the invention is to provide an ablation apparatus that includes a printed circuit.

Still a further object of the invention is to provide an ablation apparatus that includes a printed circuit which monitors impedance, temperature, circuit continuity, and is capable of multiplexing.

Another object of the invention is to provide an ablation apparatus including a conforming member made of a foam type substance.

Yet another object of the invention is to provide an ablation apparatus with an inflatable member, such as a balloon, which houses an electrolytic solution that selectively flows out of an interior of the balloon and is delivered to a desired tissue site.

Still a further object of the invention is to provide an ablation apparatus that includes a microporous membrane.

These and other objects are achieved with an ablation apparatus for ablating an inner layer of an organ in the body. An inflatable member, such as a balloon, has an interior which houses an electrolytic solution. The balloon has a back side, and a front side that includes a plurality of apertures from which electrolytic solution is permitted to selectively flow from the interior, through one of apertures, at a flow rate that is dependent on the pressure applied to the balloon by the electrolytic solution. A conforming member, with a conductive surface and a back side, is made of a material that substantially conforms to a shape of the inner layer of the organ. Electrolytic solution and RF energy are delivered through the conductive surface to the inner layer. A printed circuit is positioned in or on the conforming member and delivers RF energy to selected sections of the inner layer. An electrical cable connects the printed circuit to an RF energy source, and an electrolytic solution delivery tube delivers electrolytic solution from an electrolytic solution source to and from the balloon.

A membrane can be included and positioned between the front side of the balloon and the back side of the conforming member. The membrane includes a plurality of apertures for receiving electrolytic solution from the balloon and delivering it to the conforming member and the inner layer of the organ.

In another embodiment of the invention, the balloon is made of a material that includes a plurality of apertures around its entire surface. The conforming member is in a surrounding relationship to the balloon, and a membrane positioned between the balloon and the conforming member. Electrolytic solution and RF energy are delivered through the conductive layer of the conforming member which is generally in contact with substantially the entire interior of a body organ, or a selected section of the body organ.

The flow rate of electrolytic solution leaving the balloon, including but not limited to saline solution, is adjustable and depends on the pressure applied by the electrolytic solution to the balloon, typically caused by increasing or decreasing the amount of electrolytic solution in the balloon. The membrane is microporous, and the conforming member, which typically is a layer of a foam type material, both provide a controlled flow of electrolytic solution to the inner wall of the body organ. Additionally, the foam material of the conforming member is particularly pliable and suitable for conforming to the inner wall, and achieves an effective ablation of all or a part of the inner wall even when it has a very irregular surface.

An important consideration of the invention is that the conforming member provides a conductive surface that conforms to surfaces that have irregular shapes. The combinations of the printed circuit, conforming member and electrolytic solution provide for delivery of RF energy. Thus, RF energy can be effectively delivered to irregular surfaces.

Additionally, the printed circuit, which may be in the conforming member, on its back surface, or on its conductive surface, is segmented. The printed circuit is multiplexed and capable of monitoring impedance, temperature and circuit continuity.

The ablation apparatus of the invention is suitable for ablating a variety of surfaces of body organs including but not limited to the endometrium of the uterus.

DESCRIPTION OF THE DRAWINGS

Housed in the introducer sheath are viewing and illumination fibers, a tension wire, an RF cable and an electrolytic solution tube.

DETAILED DESCRIPTION OF THE PREFERRED EMBODIMENTS

Figures 1A, 1B, 1C:
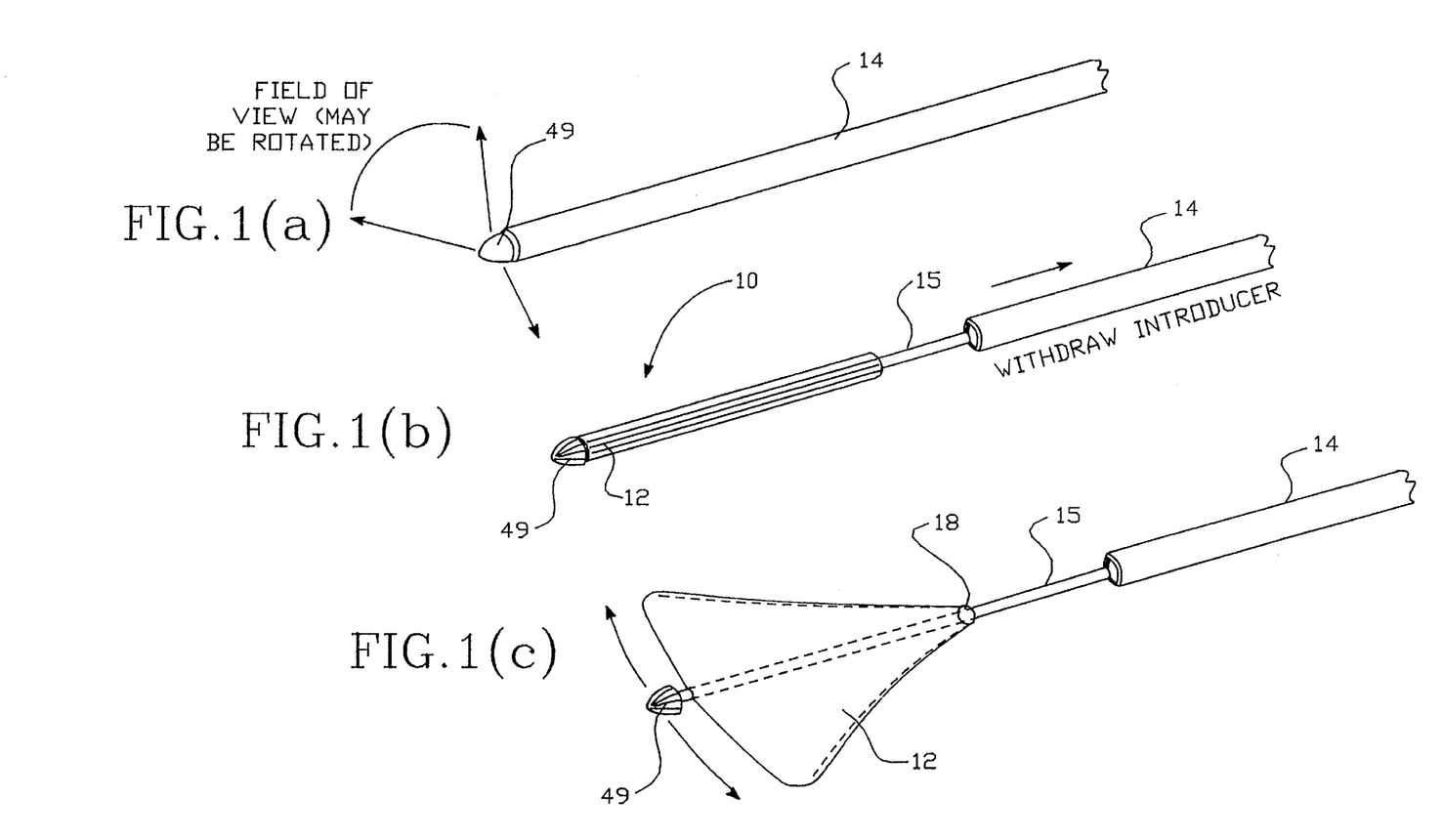
FIG. 1(a) is a perspective view of an ablation apparatus of the invention housed in an introducer sleeve and includes viewing optics.
FIG. 1(b) is a perspective view of an ablation device of the invention in a non-deployed position as the introducer sleeve is withdrawn.
FIG. 1(c) is a perspective view of an ablation device of the invention in a deployed position.
Figure 1D:
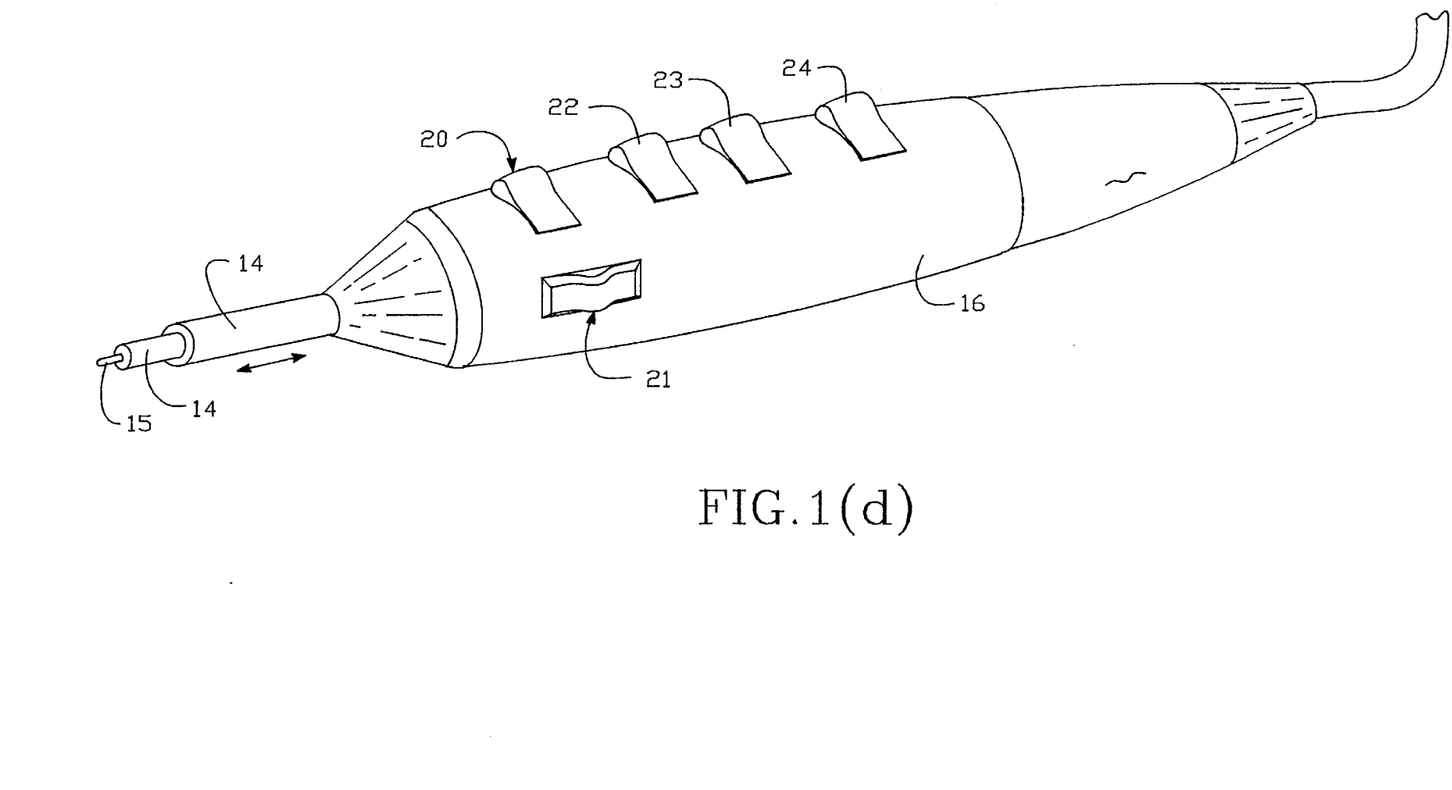
FIG. 1(d) is a perspective view of a handle associated with the ablation device of the invention.

An ablation apparatus 10 of the invention is illustrated in FIG. 1(a), 1(b) and 1 (c) and includes an inflatable member 12, including but not limited to a balloon, that is introduced into a desired body organ through an introducer sleeve 14 which can be attached to a handpiece 16 (FIG. 1(d)). Balloon 12 is rolled or folded around a core lumen 15 which contains optics, fluid paths, sensor and electronic cabling and can be attached to a ratchet hinge 18 which imparts movement of balloon 12 when it is in a body organ. Balloon 12 is introduced through introducer sleeve 14 in a folded, or non-distended configuration. Formed spring wires can be included in balloon 12 to assist in opening it to the deployed position. Included on handle 16 are a variety of actuators 20 through 24 which provide physician control of ablation apparatus 10, as more fully described hereafter. The actuators can be rocker switches, slider switches and the like. Ablation apparatus 10 is sufficiently opqaue that it is visible under ultra sound.

Introducer sleeve 14 is introduced into the desired organ, as shown in FIG. 1(a), with balloon 12 in a non-deployed configuration. Following induction, introducer sleeve 14 is withdrawn and can be retracted into handle 16. Introducer sleeve 14 can be of conventional design, such as an introducing catheter, well known to those skilled in the art. Balloon 12 can be swept from side to side, which movement is imparted by hinge 18.

Generally, ablation apparatus 10 can be a mono-polar or bi-polar electrode system which is capable of expanding so that balloon 12 becomes inflated within a selected body organ, and RF energy is delivered to an inner lining of the organ. RF energy is passed through the inner lining or surface for a time period selected that is sufficient to achieve the desired degree of ablation. This varies depending on the body organ. RF current flows through body tissue from a return electrode in the form of a conductive pad applied to the patient's outer skin. Maximum heating occurs where the current density is the greatest.

In one embodiment of the invention, the body organ is the uterus, and the lining is the endometrium. It will be appreciated that the present invention is not limited to the endometrium of the uterus and that other organs, including but not limited to the stomach, can also be treated with the invention.

Electric current flowing through the endometrium causes heating due to resistance of the tissue. Endometrial ablation can be accomplished as a relatively simple medical procedure with local anesthesia.

Figure 2A:
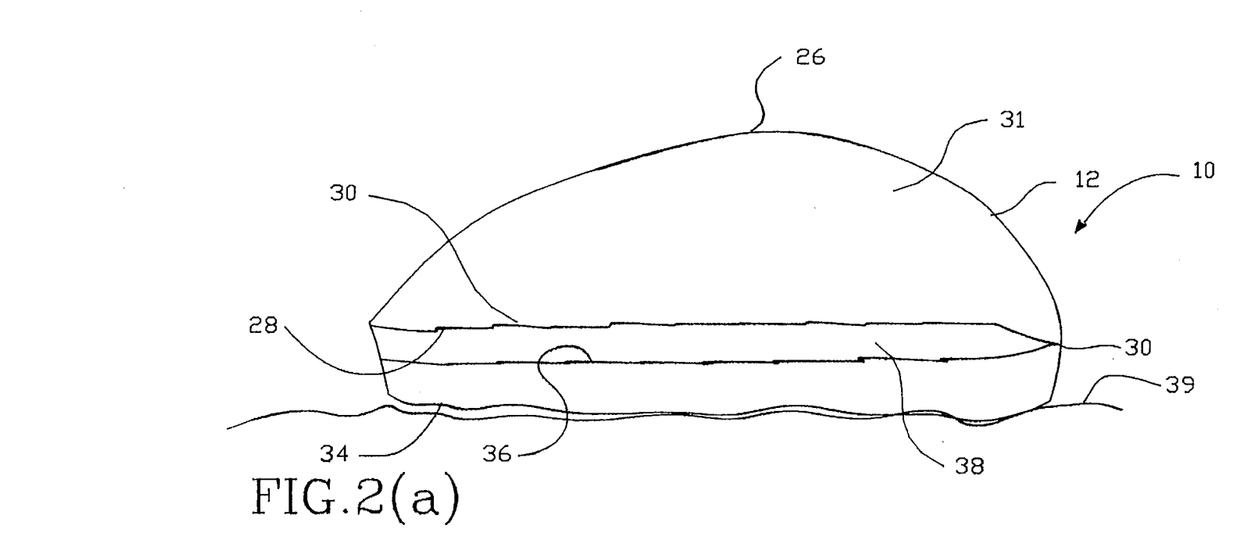
FIG. 2(a) is a cross-sectional view of an ablation apparatus of the invention with a porous membrane positioned between one side of an inflatable device and a conforming foam structure that is positioned adjacent to an inner layer of an organ.

FIG. 2(a) illustrates one embodiment of the invention with balloon 12 having a back side 26, and a front side 28 that includes a plurality of apertures 30. While a balloon, with a single interior section 31, is the preferred inflatable member, it will be appreciated that the inflatable member can be of different compositions or materials with one or more open or closed cells or chambers. The plurality of such cells or chambers can be compressed or configured in a small diameter for insertion and which will expand or be expanded after insertion to establish the desired electrical contact with the desired surface of the endometrium.

Interior 31 contains a electrolytic solution, such as saline. The amount of electrolytic fluid in interior 31 is one of the determinates for establishing the flow rate of electrolytic solution out of interior 31. Balloon 12 can become more pressurized by increasing the amount of electrolytic solution. Back side 26 presses against the interior of the uterus. As electrolytic fluid enters balloon 12, the pressure within interior 31 increases. This increases the flow rate of electrolytic solution out of apertures 30. A reduction in pressure will correspondingly reduce the flow rate.

Ablation apparatus 10 includes a conforming member 32 with a conductive surface 34 and a back side 36. Conforming member 32 is made of a material that suitably conforms to a surface 39 that is to be ablated and can have a thickness in the range of about 0.01 to 2.0 cm. Conforming member 32 can be made of a foam type material. Suitable materials include but are not limited to silicon reinforced natural gum rubber, neoprene, soft gum rubber, polyurethane, and the like. Conforming member has characteristics that make it particularly moldable to irregular surfaces. In one embodiment, conforming member 32 is made of a an open cell foam, or alternatively it can be a thermoplastic film such as polyurethane, low density polyethylene, or may be a silicone rubber. Additionally, conforming member 32 can be capable of extruding conductive materials from conforming member 32 itself. Conforming member 32 can be implanted with conductive ions, and conductive surface 34 can be coated with a material that improves its conductivity. The combination of conforming member 32 and the application of the electrolytic solution through conforming member 32 provides for the effective delivery of RF energy to the endometrium.

Optionally disposed between conforming member 32 and balloon 12 is a membrane 38 that receives electrolytic solution from balloon 12 and passes it to conforming member 32. Membrane 38 can be of the microporous type and be made of mylar, expanded PFT such as Gortex available from Gore Company. Membrane 38 is relatively strong, and sufficiently heat resistant for the amount of thermal energy that is supplied to the endometrium. Membrane 38 applies pressure relative to the electrolytic solution and thus assists in controlling its flow rate.

Figure 2B:
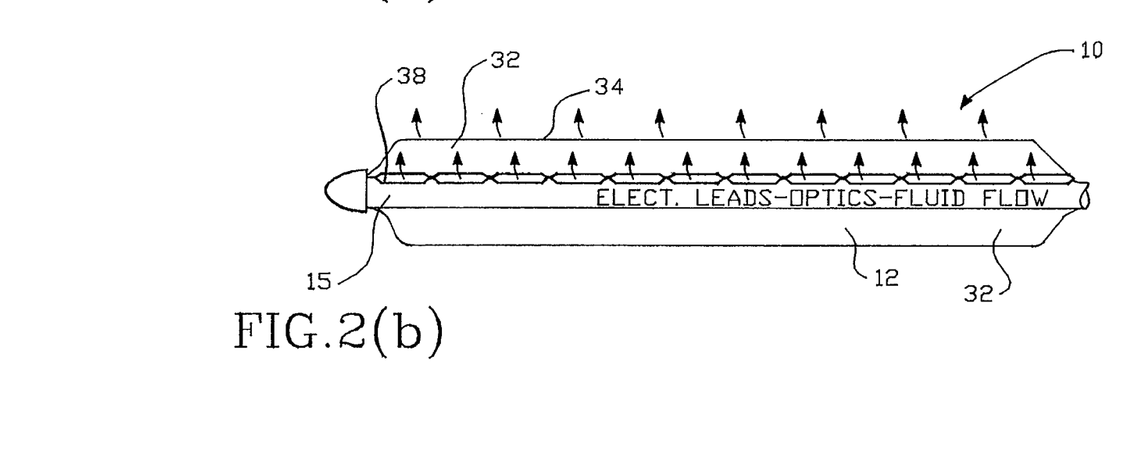
FIG. 2(b) is a cross-sectional view of an ablation apparatus of the invention and includes a core lumen that houses illumination and viewing optical fibers, fluid conduits and sensor and electronic cabling.

Membrane 38 can be a heat sealed plenum (FIG. 2(b)) to distribute electrolytic solution if conforming member is made of a foam type material. It is not needed if conforming member is a perforated film.

Figure 3:
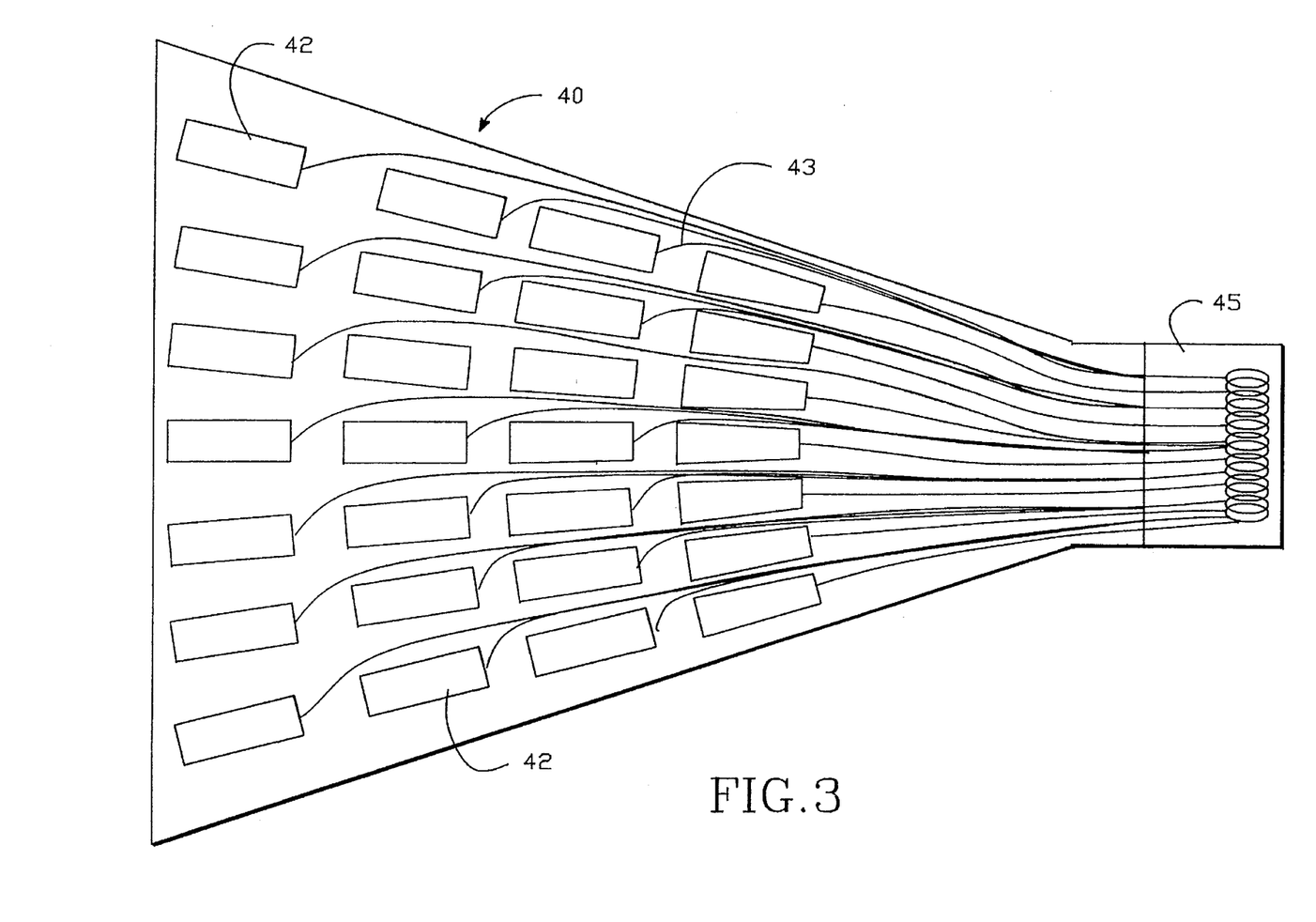
FIG. 3 is a perspective view of the invention with an inflatable device and a printed circuit that is segmented.
Figure 4:
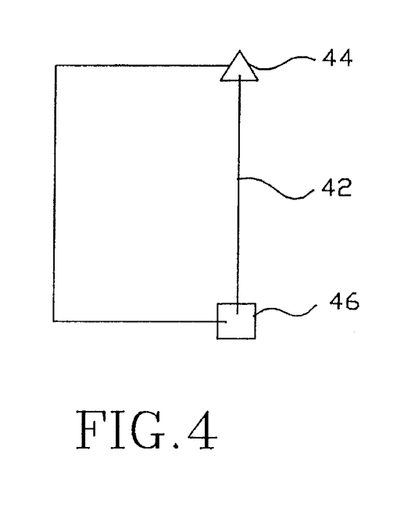
FIG. 4 is a perspective view of one of the segments of the printed circuit shown in FIG. 3.

A printed circuit 40 (FIG. 3) is deposited, etched or painted with a conductive ink in conforming member 32, at its back side 36, or on conductive surface 34. Printed circuit 40 can be formed by etching, deposition or lithography methods well known to those skilled in the art. Preferably, printed circuit 40 is located on conductive surface 34. Printed circuit 40 is formed of individual segments 42, as shown in FIG. 4, and is capable of multiplexing so that only certain segments deliver RF energy at a particular time period. Segments 42 cover the entire ablative surface. Each segment 42 connects to a separate feedwire 43, with all of the wires going to a ribbon connector 45. First, the conductive areas are "printed" and printed circuit 40 formed. Then feedwires 43 are insulated.

In one embodiment of the invention, segments 42 are about 1 cm$^2$ and are approximately 8 mm apart. Segments 42 are multiplexed, as explained in greater detail in this specification.

RF power can be sequentially supplied to each feedwire 43 in ribbon connector 45, or it can applied to only certain selected feedwires 45, enabling only selected segments 42, along with the electrolytic solution, to deliver RF energy to the endometrium. In this way, printed circuit 40 can be multiplexed. The size of individual segments included with printed circuit 40 is designed to provide the correct current density.

One or more impedance monitors 44 can be used to confirm, before an ablation event, that good coupling of energy is achieved. Also included is one or more temperature monitors/sensors 46. Temperature sensors 46 are conventional thermistors or thermocouples and are positioned on printed circuit 40. Printed circuit 40 is capable of monitoring circuit continuity in that impedance is monitored between each segment 42 and the ground electrode.

Figure 5:
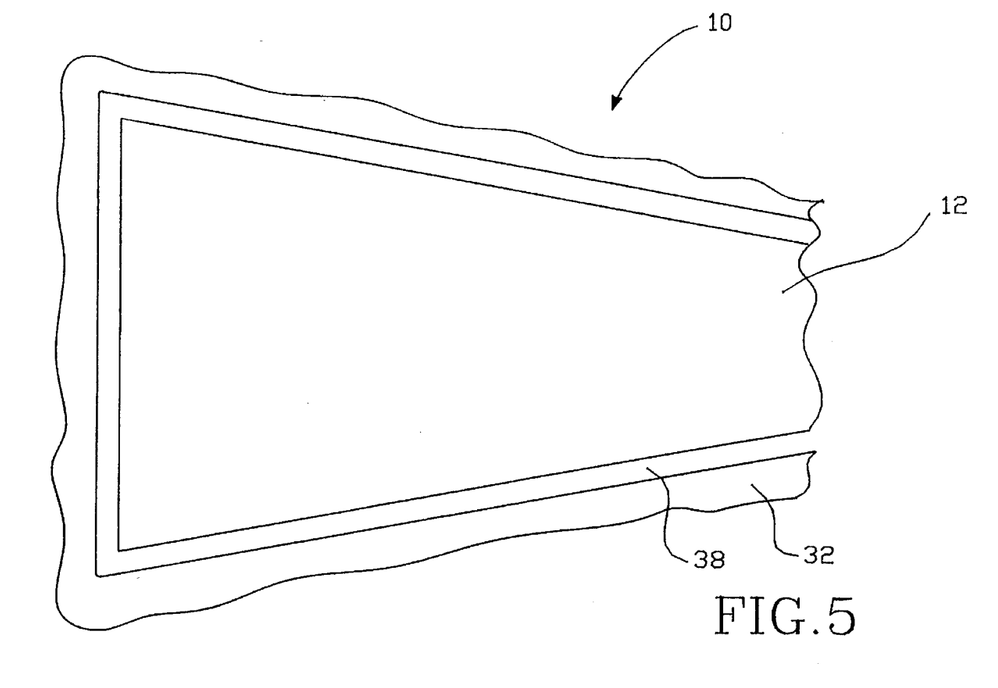
FIG. 5 is a cross-sectional view of the invention with an inflatable device surrounded by a porous membrane and a conforming foam structure.

A second embodiment of ablation apparatus 10 is illustrated in FIG. 5. In this embodiment, balloon 12 is substantially surrounded by conforming member 32. Optionally included is membrane 38. The available amount of conducting surface 34 is substantially increased. In this embodiment, ablation apparatus 10 can be configured to conform tightly with the interior of the uterus so that all, or almost all, of the endometrium is in contact with conducting surface 34. In this case, balloon 12 does not have to be moved about the uterus to complete the treatment. Alternatively, ablation apparatus 10 may not entirely fill the uterus and ablation apparatus 10 is then moved about the uterus in order to ablate all of the endometrium, or those sections where ablation is desired.

Figure 6:
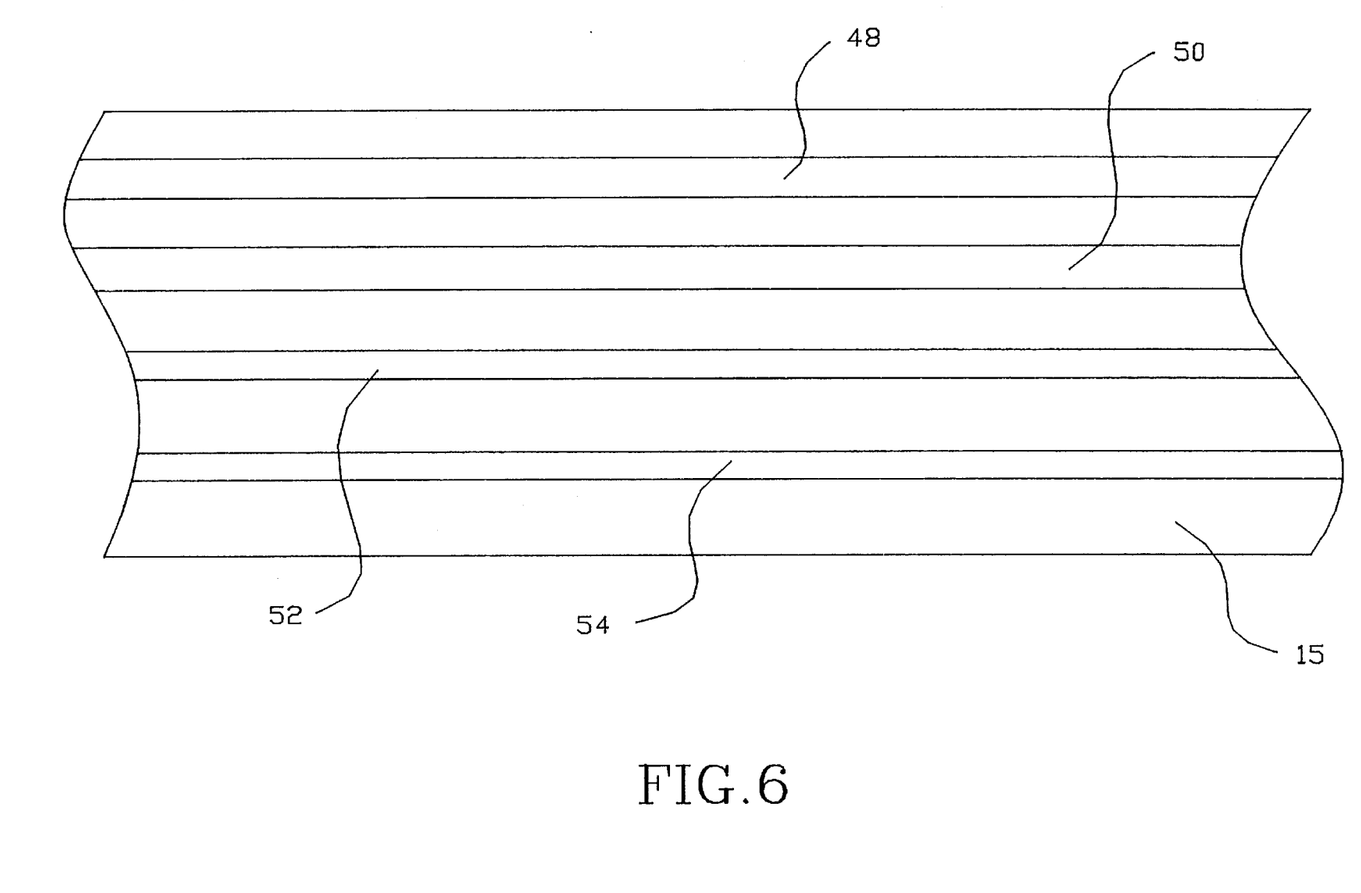
FIG. 6 is a cross-sectional view of the introducer sheath associated with the inflatable device of the invention.

In FIG. 6, a cross-sectional view of core lumen 15 shows that a variety of conduits, wires and fibers can be housed in the lumen. These include, but are not limited to viewing and illumination optical fibers 48, well known to those skilled in the art, which can deliver light, such as from a Xenon source, to viewing optics 49 (FIGS. 1(a), 1(b) and 1(c); a tension wire 50 that connects to hinge 18; an RF cable 52 connecting feedwires 43 to an RF source; and an electrolytic solution delivery conduit 54.

A two-way valve is included with delivery conduit 54. A pump or other similar device advances electrolytic solution to and from balloon 12 through delivery conduit 54. When the procedure is completed, electrolytic solution is removed from balloon 12 through delivery conduit 54. Core lumen 15 is then rotated in a twisting type of motion in order to wrap the entire ablation apparatus 10, e.g., balloon 12, conforming member 32 and membrane 38, around core lumen 15 and substantially all of the electrolytic solution is removed. Ablation apparatus 10 is then retracted back into introducer sleeve 14 and then it is removed from the uterus.

Figure 7:
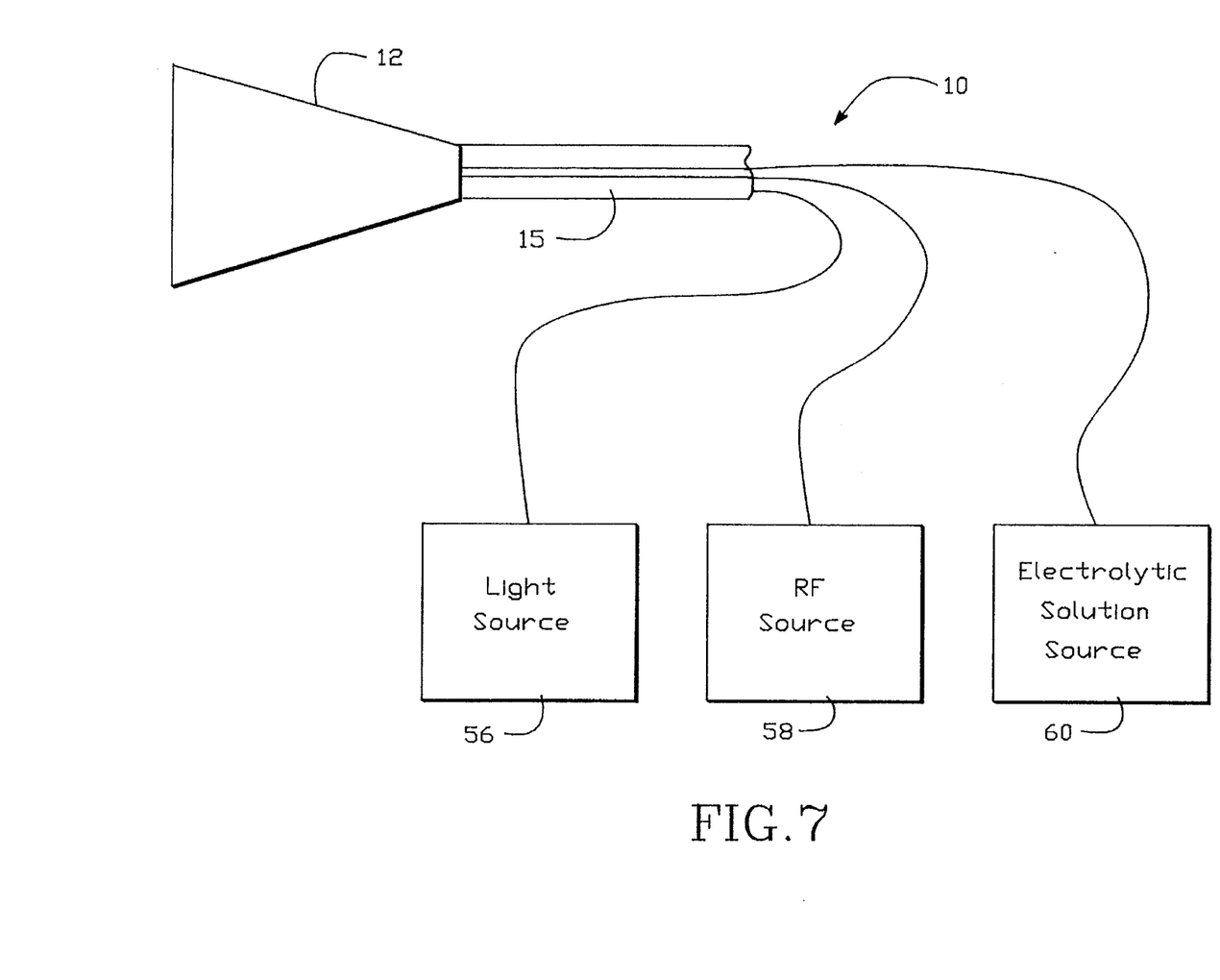
FIG. 7 is a representative block diagram of the invention showing the light, RF and electrolytic sources and their relationships to the inflatable device.

Referring now to FIGS. 1 (d) and 7, a rocker switch 20 operates the rotation and viewing of viewing optics 49. A slider switch 21 controls movement of introducer sleeve 14. Slider switch 22 is associated with tension wire 50 and is activated to cause hinge 18 to pivot and impart mechanical movement of balloon 12. Rocker switch 23 is operated by the physician to control the delivery and in certain instances the amount of RF energy from a suitable RF source 58. Finally, rocker switch 24 controls the flow of electrolytic solution to and from balloon 12 to an electrolytic solution source 60. It will be appreciated that a video camera system can be associated with handle 16.

Figure 8:
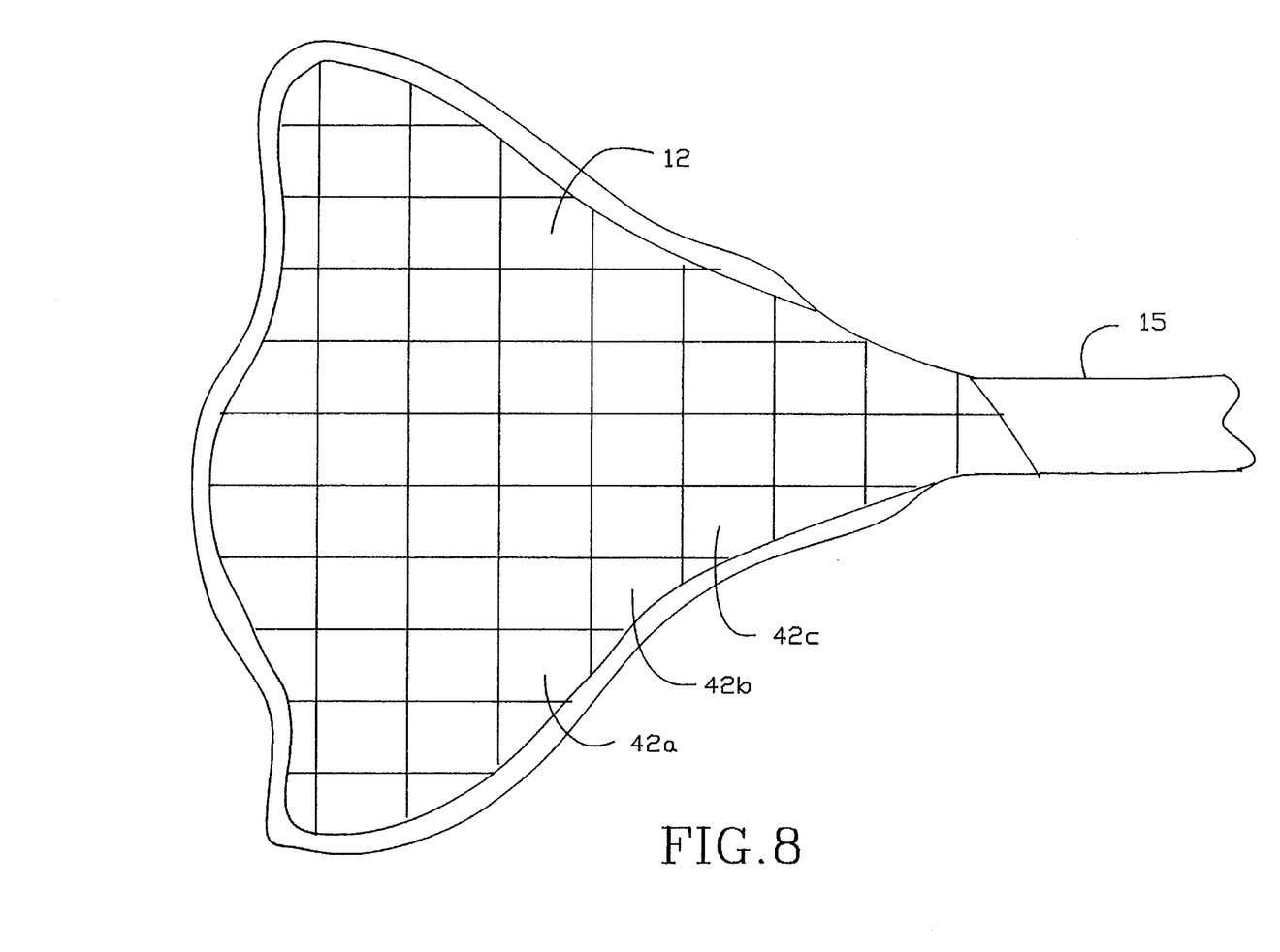
FIG. 8 is a diagram illustrating the positioning of the inflatable device of the invention in the uterus.

As previously mentioned, ablation apparatus 10 can be used with a variety of different body organs. In FIG. 8, ablation apparatus 10 is positioned in the uterus. Individual or a plurality of segments 42 can be activated to ablate the endometrium. It can deliver RF energy to only certain sections of the endometrium so that, for instance, segment 42(*a*) is first activated, then segment 42(*b*), segment 42(*c*) and so on. For example, each segment can provide 50 watts or less of power.

Figure 9:
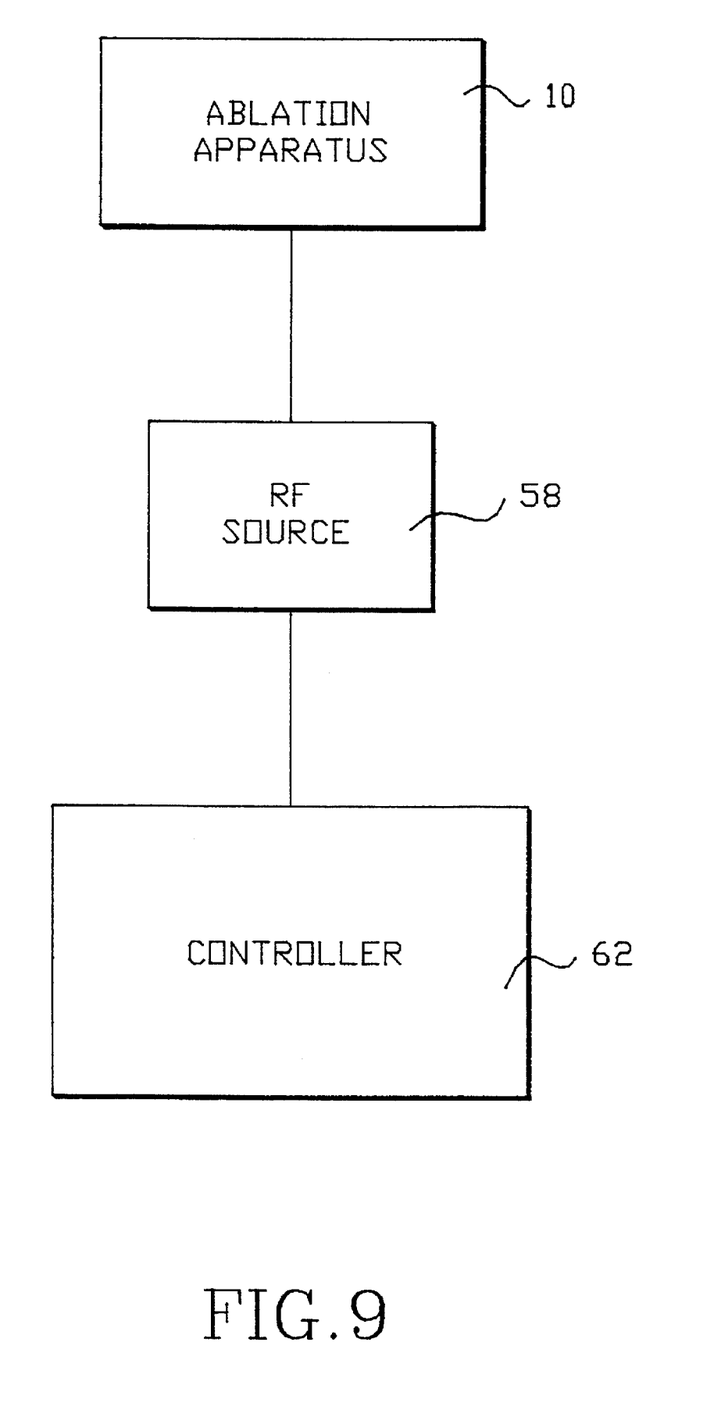
FIG. 9 is a block diagram of an ablation apparatus of the invention that includes a controller.

Referring now to FIG. 9, a controller 62 is associated with RF source 58. Controller 62 can be a digital or analog controller, or a computer with software. When controller 62 is a computer it can include a CPU coupled through a system bus. On this system are a keyboard, a disk drive, or other non-volatile memory systems, a display, and other peripherals, as known in the art. Also coupled to the bus are a program memory and a data memory.

Temperature sensors 46 and sensors contained within RF source 58 measure voltage and current that is delivered to the endometrium. The output for these sensors is used by controller 62 to control the delivery of RF power. Controller 62 also can control temperature and power. An operator set level of power and/or temperature may be determined and this will not be exceeded. Controller 62 maintains the set level under changing conditions. The amount of RF energy delivered controls the amount of power. A profile of power delivered can be incorporated in controller 62, as well as a pre-set amount of energy to be delivered can also be profiled.

Feedback is the measurement of impedance and occurs either at controller 62 or at RF source 58. This can be achieved by supplying a small amount of nontherapeutic RF energy. Voltage and current are then measured to confirm electrical contact.

Circuitry, software and feedback to controller 62 result in full process control and are used to change, (i) power (modulate)—including RF, incoherent light, microwave and the like, (ii) the duty cycle (on-off and wattage), (iii) mono-polar or bi-polar energy delivery, (iv) fluid (electrolyte/saline) delivery, flow rate and pressure and (v) determine when ablation is completed through time, temperature and/or impedance. These process variables can be controlled and varied based on tissue temperature monitored at multiple sites on the ablating surface, and impedance to current flow monitored at each segment 42, indicating changes in current carrying capability of the tissue during the ablative process.

Additionally, controller 64 can provide multiplexing, monitor circuit continuity, and/or determine which segment 42 of printed circuit 40 is activated.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

I claim:

1. An ablation apparatus for ablating an inner layer in an organ of a body, comprising:

an inflatable member with an interior housing an electrolytic solution, the inflatable member having a back side, and a front side with a plurality of apertures that permit electrolytic solution to selectively flow from the interior through the plurality of apertures at a flow rate dependent on a pressure applied to the inflatable member by the electrolytic solution;

a conforming member with a conductive surface and a back side connected to the front side of the inflatable member, the conforming member being made of a material that substantially conforms to a shape of the inner layer of the organ and delivers electrolytic solution and RF energy through the conductive surface to the inner layer, a printed circuit positioned on the conforming member delivering RF energy to selected sections of the inner layer;

an electrical connector device connecting the printed circuit to an RF energy source; and an electrolytic solution delivery tube to deliver electrolytic solution from the electrolytic solution source to and from the inflatable member and into the conforming member.

2. The ablation apparatus of claim 1, wherein the inflatable member is a balloon.

3. The ablation apparatus of claim 1, further comprising:

a membrane positioned between the front side of the inflatable member and the back side of the conforming member, the membrane adapted to receive electrolytic solution from the inflatable member and delivering the electrolytic solution to the conforming member.

4. The ablation apparatus of claim 1, wherein the conforming member is made of an open and closed cell foam.

5. The ablation apparatus of claim 1, wherein the printed circuit is multiplexed.

6. The ablation apparatus of claim 1, wherein the printed circuit includes one or more impedance sensors positioned on the conforming member.

7. The ablation apparatus of claim 6, wherein the printed circuit includes one or more temperature sensors positioned on the conforming member.

8. The ablation apparatus of claim 7, wherein the printed circuit includes one or more devices to monitor circuit continuity.

9. The ablation apparatus of claim 8, wherein the printed circuit includes a plurality of segments.

10. The ablation apparatus of claim 1 each segment delivers about 50 watts of energy or less to a section of the inner layer.

11. The ablation apparatus of claim 1, wherein the conforming member releases a conductive material contained within the conforming member to the inner layer.

12. The ablation apparatus of claim 1, further comprising:

a deposition of ions in the conforming member to improve conductivity.

13. The ablation apparatus of claim 1, further comprising:

conductive coating on the conductive surface of the conforming member.

14. An ablation apparatus for ablating an inner layer in an organ of a body, comprising:

an inflatable member with an exterior surface including a plurality of apertures that communicate with an interior that houses an electrolytic solution, the inflatable member selectively releasing electrolytic solution through the apertures at a flow rate that is dependent on a pressure applied to the inflatable member by the electrolytic solution;

a conforming member with a conductive surface, and a back side in surrounding relationship and attached to the exterior of the inflatable member, the conforming member being made of a material that provides substantial conformity between the conductive surface and a shape of the inner layer of the organ, the conductive surface delivering electrolytic solution and RF energy to the inner layer;

a printed circuit positioned on the conforming member delivering RF energy to selected sections of the inner layer;

an electrical connector device connecting the printed circuit to an RF energy source; and an electrolytic solution delivery tube to deliver electrolytic solution to the inflatable member from an electrolytic solution source and into the conforming member.

15. The ablation apparatus of claim 14, wherein the inflatable member is a balloon.

16. The ablation apparatus of claim 14, further comprising:

a membrane positioned between the inflatable member and the conforming member and adapted to receive electrolytic solution from the inflatable member and deliver it to the conforming member.

17. The ablation apparatus of claim 14, wherein the conforming member is made of an open and closed cell foam.

18. The ablation apparatus of claim 14, wherein the printed circuit is multiplexed.

19. The ablation apparatus of claim 14, wherein the printed circuit includes or more impedance sensors positioned on the conforming member.

20. The ablation apparatus of claim 19, wherein the printed circuit includes one or more temperature sensors positioned on the conforming member.

21. The ablation apparatus of claim 20, wherein the printed circuit includes one or more devices to monitor circuit continuity.

22. The ablation apparatus of claim 21, wherein the printed circuit includes a plurality of segments.

23. The ablation apparatus of claim 22, wherein each segment delivers about 50 watts of energy or less to a section of the inner layer.

24. The ablation apparatus of claim 14, wherein the conforming member releases a conductive foam contained within the conforming member to the inner layer.

25. The ablation apparatus of claim 14, further comprising:

a deposition of ions in the conforming member to improve conductivity.

26. The ablation apparatus of claim 14, further comprising:

conductive coating on the conductive surface of the conforming member.

27. The ablation apparatus of claim 14, wherein the electrolytic solution is a saline solution.

28. An ablation apparatus for ablating an inner layer in an organ of a body comprising:

a first expandable member;

a second expandable member surrounding the first expandable member and attached thereto, the second expandable member having a porous structure to deliver an electrolytic solution to the inner layer of the organ;

a plurality of RF electrodes positioned at one of an exterior of the first expandable member or an interior of the second expandable member:

an electrical connector device connecting the plurality of RF electrodes to an RF energy source; and an electrolytic solution delivery device connected to deliver electrolytic solution to the interior of the second expandable member and wherein the second expandable member expands to conform to at least a portion of the inner layer of the organ.

29. An apparatus as recited in claim 28 wherein the second expandable member expands in response to the delivery of the electrolytic solution.

* * * * *